United States Patent [19]

Ahlers et al.

[11] Patent Number: 5,674,531
[45] Date of Patent: Oct. 7, 1997

[54] NANOPARTICLES CONTAINING AN ACTIVE SUBSTANCE AND A KETALIZED POLYTARTRAMIDIC ACID, PROCESS FOR THEIR PREPARATION, AND USE THEREOF

[75] Inventors: Michael Ahlers, Mainz; Axel Walch, Frankfurt am Main; Gerhard Seipke, Hofheim, all of Germany; Gregory Russell-Jones, Middel Cove, Australia

[73] Assignee: Hoechst Aktiengesellschaft, Frankfurt am Main, Germany

[21] Appl. No.: 399,474

[22] Filed: Mar. 7, 1995

[30] Foreign Application Priority Data

Mar. 9, 1994 [DE] Germany ............ 44 07 898.6

[51] Int. Cl.$^6$ ............ A61K 9/14; A61K 9/51
[52] U.S. Cl. ............ 424/489; 424/490; 424/491; 514/808; 514/951
[58] Field of Search ............ 424/489, 490, 424/491

[56] References Cited

U.S. PATENT DOCUMENTS

| | | | |
|---|---|---|---|
| 3,297,033 | 1/1967 | Schmitt et al. | 128/335.5 |
| 3,773,919 | 11/1973 | Boswell et al. | 424/19 |
| 4,093,709 | 6/1978 | Choi et al. | 424/19 |
| 5,391,696 | 2/1995 | Krone et al. | 528/288 |

*Primary Examiner*—Thurman K. Page
*Assistant Examiner*—James M. Spear
*Attorney, Agent, or Firm*—Finnegan, Henderson, Farabow, Garrett & Dunner, L.L.P.

[57] ABSTRACT

Nanoparticles containing an active substance and a ketalized polytartramidic acid, process for their preparation, and use thereof. Nanoparticles containing an active substance and a ketalized polytartramidic acid are suitable as vehicles for active substances, in particular for peptides and proteins. Processes for the preparation of the nanoparticles are described.

11 Claims, No Drawings

NANOPARTICLES CONTAINING AN ACTIVE SUBSTANCE AND A KETALIZED POLYTARTRAMIDIC ACID, PROCESS FOR THEIR PREPARATION, AND USE THEREOF

The invention relates to nanoparticles containing an active substance and a ketalized polytartramidic acid, which are suitable as vehicles for active substances, in particular for peptides or proteins.

In biodegradable pharmaceutical delivery systems, such as specified in U.S. Pat. No. 4,093,709, the active compound is dispersed in a biodegradable polymer which releases the active substance on degradation. Typical biodegradable polymers investigated most according to the prior art are homo- and copolyesters, in particular of lactic and glycolic acid, such as are described in U.S. Pat. No. 3,773,919 and U.S. Pat. No. 3,297,033. Disadvantages are, inter alia, the poorly controllable swellability of the polyester in the physiological medium and the complex mechanism of active substance release associated therewith. In general, after an appreciable "initial burst", only a small to moderate release rate is additionally produced.

Ketalized polytartramidic acids are also described in EP 0 514 790. Using the process described there, however, no success was achieved in preparing nanoparticles which contain an active substance.

In addition to protection from hydrolysis and a suitable release profile, oral administration forms should also promote the absorption of the active substance through the intestinal wall. Targeted release in the intestinal lumen from capsules which are enteric-coated does prevent acidic hydrolysis in the stomach, but can lead to peptide and protein active substances being subjected to degradation as a result of digestion. Examples of such release forms are capsules made of polyacrylic derivatives having pH-dependent coatings (Rubinstein et al. Int. J. Pharm. 30, 95–99, 1986) and capsules having azoaromatic film coatings which are bacterially degraded (Saffran et al. Science, 233, 1081–1084, 1986).

A modern pharmaceutical therapy requires an administration form which guarantees a controlled release rate of active substance. Particularly for highly active peptide and protein active substances, a uniform release is necessary over long periods of time.

The object of the present invention is to prepare nanoparticles which are biocompatible and degradable and suitable as vehicles, in particular for peptide and protein active substances, and serve as a release and transport system.

It has now been found that, from ketalized polytartramidic acids of the formula I and active substances, nanoparticles can be prepared which are suitable for use as transport and release systems for the administration of pharmaceuticals.

Surprisingly, the formulation of active substance-containing nanoparticles from these polymers was carried out as a prerequisite for gastrointestinal, nonspecific absorption. It is additionally possible to functionalize these active substance-containing nanoparticles with coupling groups to which specific ligands can be bound which make possible receptor-mediated transport through the intestinal wall. Specific ligands can also be incorporated directly into the nanoparticle surface.

The invention therefore relates to nanoparticles containing an active substance and a ketalized polytartramidic acid which essentially contains at least 95 mol % of recurring structural units of the formula I

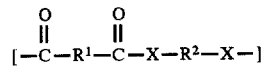

where $R^1$ is the radical of the formula II

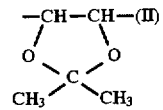

X is —NH—, and $R^2$ is straight-chain or branched alkyl or cycloalkyl which can be substituted by one or more inert radicals.

The term "inert radical" is understood as meaning substituents which do not react with one another under the preparation and processing conditions of the ketalized polytartramidic acids or are prevented from reacting with one another by protective groups thereon. Inert radicals can be, for example, inorganic radicals, such as halogen, or they can be organic radicals such as alkyl, alkenyl, cycloalkyl, cycloalkenyl, alkoxy or dialkylaminoalkyl.

Functional groups which are prevented from reaction by protective groups are, for example, amino or hydroxyl.

Known protective groups are the benzyloxy or phenylsulfonyl groups. The term active substance is understood as meaning active substances based on carbohydrates, peptides and proteins, e.g. insulin, calcitonin or buserelin.

Nanoparticles are spherical particles having a diameter of 10 to 1000 nm, preferably of 50 to 800 nm, in particular of 200 to 600 nm.

Preferably, ketalized polytartramidic acids of the formula I which essentially contain at least 95 mol % of recurring structural units of the formula I, where
$R^1$ is the compound of the formula II,
X is —NH— and
$R^2$ is
  a) straight-chain or branched alkyl or alkenyl, having 1 to 18 carbon atoms or
  b) straight-chain or branched alkyl or alkenyl, having 1 to 18 carbon atoms, substituted one or more times by a radical from the group consisting of:
    1) carboxyl or
    2) carboxyl in which the hydroxyl group is replaced by a radical from the group consisting of:
      2.1 —O—($C_1$–$C_{18}$)-alkyl, straight-chain or branched,
      2.2 —O—($C_3$–$C_{18}$)-cycloalkyl,
      2.3 ($C_1$–$C_6$)-alkylamino or
      2.4 ($C_1$–$C_6$)-alkylamino, substituted one or more times in the alkyl moiety by a radical from the group consisting of:
        2.4.1 hydroxyl or
        2.4.2 —O—($C_2$–$C_4$)-alkyl,
are employed in the nanoparticles.

Particularly preferably, polycondensates of the formula I which essentially contain at least 95 mol % of recurring structural units of the formula I are employed in the nanoparticles, where
$R^1$ is the compound of the formula II,
X is —NH— and
$R^2$ is
  a) alkyl having 1 to 18 carbon atoms,
  b) ($C_3$–$C_8$)-cycloalkyl or c) the radical of the formula III

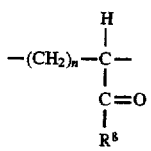
(III)

where n is 3 or 4 and $R^6$ is $(C_1-C_{18})$-alkoxy.

To prepare the ketalized polytartramidic acids of the formula I, dimethyl 2,3-isopropylidenetartrates are reacted with one or more of the diamines of the formula IV

(IV)

where $R^2$ has the abovementioned meaning.

It is obvious to the person skilled in the art that the sum of all structural units derived from the dimethyl 2,3-isopropylidenetartrate (A) and the sum of all structural units derived from the various diamines (B) are essentially identical. Hence the amounts of (A) and (B) differ by a maximum of about 1%, preferably a maximum of about 0.2%; in particular they are identical within the framework of the practical measurement and dose possibilities.

The molecular weight of the resulting ketalized polytartramidic acids can be controlled, inter alia, by means of the selection of the quantitative ratios of A to B. These selection criteria are known to the person skilled in the art in the field of polycondensation.

Examples of suitable diamines of the formula IV are 1,6-diaminohexane, 1,8-diaminooctane, trans-1,4-diaminocyclohexane or 1,12-diaminododecane.

The condensation of the components described above is in general carried out in solution. To do this, monomeric compounds to be reacted with one another are as a rule dissolved in an organic solvent. The organic solvent in this case preferably contains at least one solvent, e.g. N-methyl-2-pyrrolidone or toluene.

The synthesis of the ketalized polytartramidic acids of the formula I is carried out in two stages starting from tartaric acid and diamine. The first stage of the dimethyl isopropylidenetartrate can be prepared directly from tartaric acid and 2,2-dimethoxypropane without isolation of the intermediate isopropylidenetartaric acid.

The polycondensation of dimethyl isopropylidenetartrate with diamines is carried out with elimination of methanol. The use of a catalyst or auxiliary reagent for this is unnecessary. Since the exothermic reaction of the starting materials starts even at room temperature, to achieve a high molecular weight attention has to be paid to keeping exactly to the molar ratios of the reactants.

To carry out the solution polymerization, high-boiling solvents such as N-methylpyrrolidone or toluene are used. The reaction is carried out, for example, at from 80° to 140° C. The resulting methanol is removed by azeotropic distillation or bypassing in a stream of $N_2$.

Melt condensation, which can be carried out with the tartaric acid methyl esters despite the ketal groups and leads to homogeneous products in an elegant and simple manner, is a particular advantage.

For this, the reactants are first stirred for 1 to 6 hours (h) at temperatures from 30° to 80° C. in order to prevent the escape of one of the monomer components. The mixture is then heated under reduced pressure for 8 to 16 h at 80° to 120° C. For working up, the polymers are customarily dissolved in dichloromethane and precipitated in suitable precipitating agents such as diisopropyl ether.

In the course of the polycondensation, the molecular weight of the polymer and thus also the viscosity of the reaction mixture increases. Molecular weights of 1000 to 100,000 are reached, preferably 5000 to 40,000. As a rule, viscosities of more than 0.1 dl·g$^{-1}$ (Staudinger index, dimethylformamide, 25° C.) are reached.

The construction of the ketalized polytartramidic acids makes possible good control of the degradability, as hydrolysis can take place both via the side groups and via the main chain.

The rigid structure of the ketalized polytartramidic acids obtained is produced by the ketal ring of the tartaric acid and imparts to the polymers the property, in spite of the hydrogen bond-forming amide structure, of forming solid, water-insoluble forms, especially particles, which can even still absorb water-soluble components such as proteins without the form changing to soft, tacky aggregates, as is often observed with other polyamides.

Success has even been achieved in decreasing the size of the particles to the nanometer range with retention of the properties necessary for transport systems, in particular the high loading capacity, the low tendency for aggregation in solution, and the stability of the dried nanoparticles and their resuspensibility. Moreover, these nanoparticles can absorb further components having very hydrophilic groups, such as polyamines, polyhydroxycarboxylic acids and polymeric fluorescent markers without losing their defined particulate form.

The nanoparticles are prepared by coacervation or spray-drying.

In coacervation, ketalized polytartramidic acids and active substances are dissolved separately, combined to give a homogeneous solution and precipitated in a precipitating agent to give nanoparticles. The active substance is in this case included in the polymer matrix. When using peptide and protein active substances, solvents and precipitating agents are used which do not lead to any adverse effects on the active substance, e.g. by denaturation.

A 0.5 to 10% strength, preferably 3% strength, solution of the ketalized polytartramidic acids of the formula I in acetone, methanol or ethanol is thus mixed in the ratio 1:1 with a 1.5% strength solution of a peptide or protein, e.g. insulin, in methanol/water or ethanol/water having a pH of 2 to 4 and water is introduced at a temperature of 15° to 40° C. in a 2- to 10-fold, preferably 5-fold, volume by means of a cannula having an outer diameter of 0.2 to 1.2 mm. The end of the cannula is located directly above the surface of the water. The volume of the droplets obtained is 0.0005 to 0.01 ml, preferably 0.001 to 0.005 ml. During the course of this the initial mixture is rapidly stirred, the stirring element rotating at about 1000 revolutions per minute (1000 rpm). The nanoparticle suspension obtained is adjusted to pH 7 with NaOH and centrifuged. The nanoparticle fraction is resuspended in water, optionally with the addition of a suspension aid (at most 1%), centrifuged and freeze-dried. The dried nanoparticles thus obtained can be readily resuspended. It can be seen that with the ketalized polytartramidic acids of the formula I the step which is in general particularly difficult, the isolation of the nanoparticles from the suspension, is readily possible, in particular if the conditions described are kept to. In order to avoid formations of aggregates, the solvents and precipitating agents used should not be cooled and the stirring rate should clearly be below 20,000 rpm.

The size of the nanoparticles can be adjusted by means of the concentration of the polymer solution and by means of the volumetric ratio of solvent to precipitating agent. The ligand used can be vitamin $B_{12}$, vitamin $B_{12}$ analogs such as cyanocobalamin, aquocobalamin, adensosylcobalamin, methylcobalamin, hydroxycobalamin, cyanocobalamin carbanilide, 5-O-methylbenzylcobalamin, desdimethyl, monoethylamide and methylamide analogs of these compounds, analogs and homologs of cobamamide, coenzyme $B_{12}$, 5'-deoxyadenosylcobalamin, chlorocobalamin, sulfitocobalamin, nitrocobalamin, thiocyanatocobalamin, benzimidazole derivatives, adenosylcyanocobalamin, cobalamin lactone, cobalamin lactam and the anilide, ethylamide, propionamide, monocarboxylic acid and dicarboxylic acid derivatives of vitamin $B_{12}$, vitamin $B_{12}$ adipyl hydrazide or its analogs or lectins such as concanavalin A or wheatgerm lectin.

Coupling groups used are polyvinylamine or polylysine, which form covalent bonds with free carboxyl or amine groups on the surface of the nanoparticle. Furthermore, the ligand and the coupling group can additionally be bonded to one another via a spacer compound such as an alkyl radical having 1 to 18 carbon atoms, preferably 4 to 8 carbon atoms. Preferably, vitamin $B_{12}$ monocarboxylic acid is coupled to the nanoparticles via an adipyl hydrazide. To prepare nanoparticles which have units which can be coupled for functionalization on the surface, polyamines, such as polyvinylamine or polylysine, and/or polyhydroxyacids such as polyaspartic acid are added to the ketalized polytartramidic acids of the formula I in concentrations of 1 to 25%. Further processing is carried out as described above.

To prepare nanoparticles by means of spray-drying, the ketalized polytartrimidic acids to be sprayed are applied in concentrations of 0.2 to 5%, preferably 0.5 to 1.5%, in pure solvents such as acetone, methanol, ethanol or dioxane and also in mixtures of these components with, if desired, a small addition of water. The active subtances in concentrations of 1 to 60%, preferably of 4 to 25% (w/w relative to ketalized polytartramidic acid), optionally FITC-labeled polymer (0.2 to 5%), or suspension aid in the range from 1 to 20%, preferably from 2 to 10%, and also basic polymer in the range from 0.5 to 30%, in particular 1 to 10%, are added to these polymer solutions.

To prepare active substance-loaded nanoparticles having a size of less than 1000 nm, the solution of polymer, active substance and optionally other additives to be sprayed must have a specific viscosity of 0.2 to 3.5, in particular 0.3 to 2.0.

Spraying is carried out at an inlet temperature of the spray drier of 40° to 110° C., preferably below 80° C., an outlet temperature of 25° to 70° C., preferably from 30° to 50° C., a flow rate of $N_2$ of 500 l/h to 800 l/h and a volume flow of 1 to 5 ml/min.

The resultant nanoparticles are collected on a closemeshed sieve fabric (nylon fabric having a pore size of 0.010mm). The particle size is from 10nm to 1000 nm and the mean value as a rule is clearly below 600nm. Depending on the composition, the particles are stored under reduced pressure for 2 to 8 h after spraying. The yield is 25 to 80%, as a rule more than 50%.

The nanoparticles obtained by the spray-drying or coacervation method can additionally be filtered for the reduction of larger particles. Suitable filters have a pore diameter of 0.2 μm to 0.8 μm, preferably 0.45 μm. Suitable membranes consist, for example, of cellulose acetate.

The particle size is determined by means of photon correlation spectroscopy (PCS), aerosol spectroscopy and electron microscopy (REM) (J. P. Fischer, Progress in Colloid and Polymer Science, 77, pages 180–194, 1988), if present the surface basicity of the nanoparticles is determined by means of polyelectrolyte titration (streaming current detector, SCD), the fluorescence content by spectroscopy and the active substance content and release of active substance by chromatography. The nanoparticles obtained have a narrow size distribution. The nonuniformity of the nanoparticles obtained (dw/dn) is from 1.1 to 2.0, in particular 1.15 to 1.5. On account of the narrow size distribution, the nanoparticles are also suitable for calibration purposes in raster electron microscopy or for the determination of the distribution of active substances in the body of animals or humans after oral administration if the nanoparticles contain a fluorescent or radioactive marker. The biodegradable particle decomposes and is excreted from the body.

EXAMPLE 1

Poly-(2,3-O-isopropylidene)-DL-tartaric acid 1',6'-hexylamide

Synthesis of dimethyl 2,3-O-isopropylidene-DL-tartrate 700 g of DL-tartaric acid and 7 g of p-toluenesulfonic acid are dissolved in 1 l (liter) of methanol with warming and treated with 1.2 l of 2,2-dimethoxypropane slowly such that the tartaric acid no longer precipitates. The mixture is boiled under reflux for 5 h. The resulting acetone is then distilled off continuously and slowly (distillate: 53% acetone, 38% methanol, 11% dimethoxypropane). A further 320 ml of 2,2-dimethoxypropane are added to the mixture and the tartaric acid is reacted completely to give the dimethyl ester. After completion of the reaction (altogether 15 h), the methanol is distilled off with the residues of dimethoxypropane and acetone. 700 ml of 2,2-dimethoxypropane and 1 l of cyclohexane are added to the residue. The azeotrope with cyclohexane resulting by formation of methanol is distilled off very slowly and continuously at 54° C. 540 ml of 2,2-dimethoxypropane and 820 ml of cyclohexane are subsequently added in portions. After completion of the reaction (TLC checking), the mixture is neutralized with 10 g of dried potassium carbonate and fractionally distilled. The product passes over at 95° C. and 0.1 mbar. Yield: 972 g Poly-(2,3-O-isopropylidene)-D,L-tartaric acid 1',6'-hexylamide 1,6-Diaminohexane is melted and weighed in the exact molar ratio (7.814 g, 60 mmol) into dimethyl 2,3-O-isopropylidene-D,L-tartrate (13.094 g, 60 mmol). After addition of 15 ml of N-methylpyrrolidone, the mixture is stirred at 120° C. for 4 days under $N_2$. During this time, 20 ml of toluene each time are added 5 times and distilled off together with the methanol formed. After addition of dichloromethane, precipitation is carried out twice in ice-cooled diisopropyl ether. The polymer formed is dried to constant weight at 40° C. under reduced pressure. Yield: 13.7 g Softening point $T_g$: 96° C.

EXAMPLE 2

Poly-2,3-O-isopropylidene-L-tartaric acid 1',4'-cyclohexylamide co-1',12'-dodecylamide (1:1)

trans-1,4-Diaminocyclohexane (2.853 g, 24.98 mmol), 1,12-diaminododecane (5.00 g, 24.98 mmol) and dimethyl 2,3-O-isopropylidene-L-tartrate (10.91 g, 49.97 mol) are weighed directly into a laboratory reactor. The mixture is warmed slowly to 80° C. under a gentle stream of $N_2$ and stirred at this temperature for 2.5 h. During the course of this the methanol formed distils off. The temperature is increased to 130° C. at stirring speeds from 10 to 60 rpm and the pressure is reduced to 200 mbar for 4 h and to 0.5 mbar for a further 4 h. The polymer formed is dissolved in dichloromethane, precipitated 3 times in diisopropyl ether and then dried under reduced pressure. Softening point $T_g$: 125° C.

EXAMPLE 3

Poly-2,3-O-isopropylidene-L-tartaric acid 1',8'-octylamide

Dimethyl-2,3-O-isopropylidene-L-tartrate (36.66 g, 168 mmol) and freshly sublimed 1,8-diaminooctane (24.24 g, 168 mmol) are weighed directly into a laboratory reactor. The mixture is slowly warmed to 80° C. under a gentle stream of $N_2$ and stirred at this temperature for 2.5 h. During the course of this the methanol formed distils off. The pressure at 100° C. is reduced to 200 mbar for 4 h and to 0.5 mbar for a further 4 h at stirring speeds of 10 to 60 rpm. The product is dissolved in dichloromethane, precipitated 3 times in diisopropyl ether and then dried under reduced pressure. Yield: 47.3 g Softening point $T_g$: 104° C.

EXAMPLE 4

A 3% strength solution in 1 ml of methanol is prepared using the polymer from Example 3. 15 mg of insulin are dissolved in methanol in a total volume of 1 ml using HCl (0.1 molar) at pH=2.7 and subsequent pH adjustment (using 0.1N NaOH) to 7.5. The two solutions are mixed together and added dropwise through a cannula (26G*23, Luer) having an external diameter of d=0.45 mm to 8 ml of distilled water at a rate of 0.5 ml/min.

The suspension is centrifuged at 15,000 rpm for 15 min, the supernatant is decanted and the particle fraction is taken up in 10 ml of water. The suspension is centrifuged again under the abovementioned conditions and freeze-dried after resuspension. Yield: 48% Particle diameter: less than 500 nm (according to REM)

EXAMPLE 5

A 0.5% strength solution which consists of three individual solutions which are mixed together in the sequence 1 to 3 is sprayed into a spray dryer (Mini Spray Dryer, Büchi):

| | |
|---|---|
| Solution 1: | 280 mg of polymer (Example 3), dissolved in 55 ml of methanol |
| Solution 2: | 60 mg of polylysine dissolved in 10 ml of methanol |
| Solution 3: | 40 mg of insulin dissolved in 10 ml of methanol and 0.040 ml of 1 N HCl |

This solution is sprayed under the following parameter settings:

| | |
|---|---|
| Inlet temperature | 72° C. |
| Outlet temperature | 45° C. |
| Pump rate | 3 ml/min |
| Aspirator | 10 |
| Heating | 2.9 |
| Flow | 700 |

Particle surface basicity: 70% of the amino groups employed are titratable. Diameter of the resuspended nanoparticles: 330 nm (according to PCS)

EXAMPLE 6

A mixture of the following solutions 1 and 2 is sprayed:

Solution 1: 25 mg of polymer (according to Example 3) dissolved in 10.4 ml of methanol Solution 2: 1.56 mg of insulin dissolved in 1.04 ml of methanol and 0.01 ml of 1N HCl Parameter setting on the spray dryer:

| | |
|---|---|
| Inlet temperature | 78° C. |
| Outlet temperature | 49° C. |
| Pump rate | 2 ml/min |
| Aspirator | 10 |
| Flow | 800 |

Diameter of the resulting nanoparticles (dn) 56 nm (according to PCS); dw=805 dw/dn=1.43

EXAMPLE 7

Preparation of vitamin $B_{12}$-N-hydroxysuccinimidyl ester

The preparation of a monocarboxyl derivative of vitamin $B_{12}$ is carried out by acidic hydrolysis and purification on an ion exchanger such as DOWEX® AGl-X8 (EP 0 220 030). 50 mg of the monocarboxylic acid of vitamin $B_{12}$ obtained are dissolved in 500 µl of DMSO and 15 µl of diisopropylethylamine are subsequently added thereto. The solution is stirred at room temperture under $N_2$ protective gas. A solution of 18 mg of TSTU (O-(N-succinimidyl)-N,N,N',N'-tetramethyluronium tetrafluoroborate) in 100 µl of DMF is added to this solution. The reaction solution is allowed to react at room temperature for 20 minutes. For working up, the reaction solution is diluted with 25 ml of distilled water and filtered through a 0.45 µm filter (Schleicher & Schuell disposable filtration unit, cellulose acetate membrane) and separated by means of a preparative reverse phase high-pressure liquid chromatography column (RP-HPLC columns Vydac 218TP1010; mobile phase A: 0.1% trifluoroacetic acid (TFA) in dist. water, mobile phase B: 0.1% TFA in acetonitrile: water (70:30), flow rate: 4 ml/min). The product fraction is eluted after 20–22 minutes and is then immediately frozen and lyophilized.

EXAMPLE 8

Filtration 440 mg of nanoparticles, prepared according to Example 4, are suspended in 10 ml of distilled water and filtered through a disposable filter having a cellulose acetate membrane and of pore width 0.45 µm. Yield: 385 mg, average particle diameter 320 nm.

EXAMPLE 9

Coupling of vitamin $B_{12}$ to nanoparticles 20 mg of nanoparticles, prepared according to Example 5, are suspended in 300 µl of distilled water. 3 mg of vit. $B_{12}$ TSTU ester, according to Example 7, are dissolved in 50 µl of distilled water. 0.01N NaOH is added to the suspension until a pH of 7±0.2 is attained. After this step the vit. $B_{12}$ TSTU ester is added. The suspension is stirred at room temperature for 6±0.5 hours (h). The suspension is diluted with 15 ml of distilled water and purification is carried out by repeated filtrations (0.22 µm cellulose acetate membrane, 0.8 bar ($N_2$) and medium stirring rate) using 0.5 % of polyvinylpyrrolidone 90 (BASF) (PVP90) dissolved in water as a wash solution at a temperature of 2° to 8° C. Purification can be ended if the filtrate no longer has a weak red coloration. The suspension is freeze-dried and stored at 228° C. until further use. The content of vitamin $B_{12}$ on the surface of the nanoparticles is determined by "electron spectroscopy for chemical application" using 0.03 atom percent of cobalt.

EXAMPLE 10

Coupling of $H_2NNH-C(O)-(CH_2)_4-C(O)-NHNH-C(O)$-vitamin $B_{12}$ to nanoparticles Preparation of vitamin $B_{12}$ monocarboxylic acid adipyl hydrazide Adipic acid dihydrazide and vitamin $B_{12}$ monocarboxylic acid are reacted analogously to Example 7. Purification is carried out by means of high-pressure liquid chromatography analogously to Example 7.

20 mg of nanoparticles, prepared according to Example 5, are suspended in 500 µl of DMSO and 15 µl of diisopropylethylamine are then added. The solution is stirred at room temperature under $N_2$ protective gas. A solution of 18 mg of TSTU (O-(N-succinimidyl)-N,N,N',N'-tetramethyluronium tetrafluoroborate), prepared according to Example 7, dissolved in 100 µl of dimethylformamide (DMF) is added to this solution. The reaction solution is allowed to react at room temperature for 20 minutes.

10 mg of vitamin $B_{12}$ monocarboxylic acid adipyl hydrazide (prepared as above) are dissolved in 100 µl of distilled water and added to the above reaction solution. The mixture is stirred at room temperature for 6 hours. The suspension is then diluted with 15 ml of dist. water and purification is carried out by repeated filtration (0.22 µm Millipore filter, 0.8 bar $N_2$ and medium stirring rate) using 0.5% PVP90 as a wash solution at 2° to 8° C. The retentate is lyophilized and stored at 2° to 8° C.

EXAMPLE 11

140 g of anhydroaspartic acid are suspended in 800 ml of water. 350 ml of 2 molar sodium hydroxide solution are added dropwise over a period of 5 hours such that the pH does not rise above 9.5±0.1. The reaction solution is filtered and the pH of the filtrate is adjusted to 7. The polyaspartic acid contained in the filtrate is purified several times by ultrafiltration and then lyophilized.

A 0.5% strength solution which consists of three individual solutions which are mixed together in the sequence 1 and 2 is sprayed in a spray dryer (Mini Spray Dryer, B üchi):

| Solution 1: | 1 g of polymer (according to Example 3)<br>12 mg of polyvinylamine<br>12 mg of polyaspartic acid (prepared as above)<br>Solvent 140 ml of methanol and 40 ml of dioxane |
|---|---|
| Solution 2: | 60 mg of insulin<br>Solvent 20 ml of methanol and 0.060 ml of 1 N |

This solution is sprayed under the following parameter settings:

| Inlet temperature | 80° C. |
|---|---|
| Outlet temperature | 43° C. |
| Pump rate | 2.5 ml/min |
| Aspirator | 10 |
| Flow | 800 |

Diameter of the resuspended and subsequently filtered nanoparticles is 160 nm (according to PCS).

We claim:

1. A nanoparticle containing an active substance and a ketalized polytartramidic acid which contains at least 95 mol % of recurring structural units of the formula I:

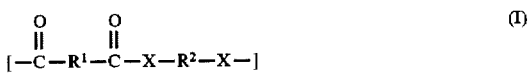

where $R^1$ is the radical of the formula (II):

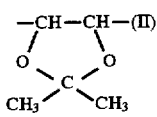

X is —NH—, and
$R^2$ is
(a) straight-chain or branched alkyl or alkenyl, having 1 to 18 carbon atoms or
(b) straight chain or branched alkyl or alkenyl, having 1 to 18 carbon atoms, substituted one or more times by a radical selected from the group consisting of:
(1) carboxyl or
(2) carboxyl in which the hydroxyl group is replaced by a radical selected from the group consisting of:
—O—($C_1$–$C_{18}$)-alkyl, straight-chain or branched,
—O—($C_3$–$C_{18}$)-cycloalkyl,
($C_1$–$C_6$)-alkylamino or
($C_1$–$C_6$)-alkylamino, substituted one or more times in the alkyl moiety by a radical selected from the group consisting of:
hydroxyl, or
—O—($C_2$–$C_4$)-alkyl wherein said nanoparticle has a diameter of 10 to 1000 nm.

2. The nanoparticle as claimed in claim 1, wherein said diameter is 200 to 600 nm.

3. A nanoparticle containing a ketalized polytartramidic acid as claimed in claim 1, where $R^1$ is the radical of the formula II,
X is —NH— and
$R^2$ is
a) alkyl having 1 to 18 carbon atoms,
b) ($C_3$–$C_8$)-cycloalkyl or
c) the radical of the formula III

where n is 3 or 4 and $R^6$ is ($C_1$–$C_{18}$)-alkoxy.

4. A pharmaceutical composition comprising nanoparticles according to claim 1.

5. The nanoparticle as claimed in claim 1, wherein the active substance content relative to the ketalized polytartramidic acid is 1 to 60%.

6. The nanoparticle as claimed in claim 1, which contains insulin, calcitonin or buserelin as the active substance.

7. The nanoparticle as claimed in claim 1, wherein ligands selected from the group consisting of vitamin $B_{12}$; cyanocobalamin; aquocobalamin; adenosylcobalamin; methylcobalamin; hydroxycobalamin; cyanocobalamin carbanilide; 5-O-methylbenzylcobalamin; and desdimethyl, monoethylamide and methylamide analogs thereof; cobamamide; coenzyme $B_{12}$, 5'-deoxyadenosylcobalamin; chlorocobalamin; sulfitocobalamin; nitrocobalamin; thiocyanotocobalamin; benzimidazole derivatives; adenosylcyanocobalamin; cobalamin lactone; cobalamin lactam; anilide, ethylamide, propionamide, monocarboxylic acid and dicarboxylic acid derivatives of vitamin $B_{12}$; vitamin $B_{12}$ adipyl hydrazide; and lectins are bonded to the nanoparticle.

8. The nanoparticle as claimed in claim 7, wherein the ligands are bonded to the nanoparticle via coupling groups selected from the group consisting of polyvinylamine, polyaspartic acid, polylysine and O-(N-succinimidyl)-N,N,N', N'-tetramethyluronium tetrafluoroborate.

9. A process for the preparation of the nanoparticles as claimed in claim 1, which comprises
   a) dissolving the active substance and the ketalized polytartramidic acid of the formula I and optionally other auxiliaries separately, mixing the solutions obtained and introducing the mixture into a precipitating agent through a cannula having an external diameter of 0.2 to 1.2 mm or
   b) separately dissolving the active substance and the ketalized polytartramidic acids of the formula I and optionally other auxiliaries, mixing the solutions obtained, the specific viscosity of the solution obtained being from 0.2 to 3.5, and spray drying the solution obtained,
   c) bonding the nanoparticles obtained by a) or b) to one or more ligands,
   d) connecting the nanoparticles obtained by a) or b) to one or more ligands via a coupling group,
   e) filtering the nanoparticles obtained by a), b), c) or d) through a filter having a pore size of 0.2 μm to 0.8 μm.

10. A process according to claim 9, wherein said nanoparticles in step (e) are filtered through a filter having a pore size of 0.45 μm.

11. A method of using the nanoparticles according to claim 1 in a pharmaceutical preparation to effect controlled delivery of active compound, said method comprising administering orally said nanoparticles to a mammal.

* * * * *

UNITED STATES PATENT AND TRADEMARK OFFICE
CERTIFICATE OF CORRECTION

PATENT NO. : 5,674,531
DATED : October 7, 1997
INVENTOR(S) : Michael Ahlers et al.

It is certified that error appears in the above-identified patent and that said Letters Patent is hereby corrected as shown below:

Claim 1, column 10, in Formula (II)

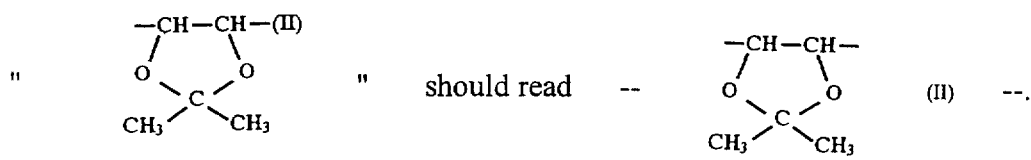

Claim 3, column 10, in Formula (III)

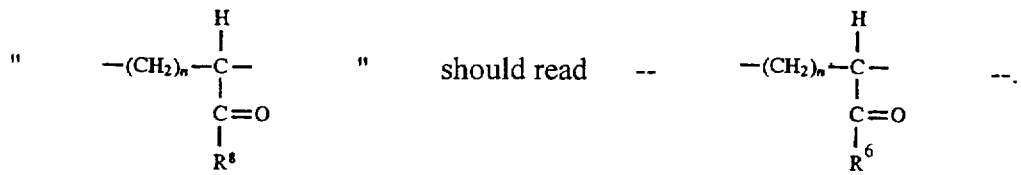

Signed and Sealed this

Twenty-eighth Day of July, 1998

*Attest:*

BRUCE LEHMAN

*Attesting Officer*   Commissioner of Patents and Trademarks